United States Patent [19]

Baumel

[11] Patent Number: 4,998,440
[45] Date of Patent: Mar. 12, 1991

[54] APPARATUS AND METHOD FOR FATIGUE TESTING A WHEEL

[76] Inventor: Stanley J. Baumel, 3400 Lagoon Dr., Burlington, Wis. 53105

[21] Appl. No.: 443,217

[22] Filed: Nov. 29, 1989

[51] Int. Cl.[5] .............................................. G01N 3/32
[52] U.S. Cl. .................................................... 73/810
[58] Field of Search .................. 73/810, 812, 849, 851

[56] References Cited

U.S. PATENT DOCUMENTS 2,761,310  9/1956  Siegel .............................. 73/812 X
2,953,018  9/1960  Volmer ................................ 73/812

*Primary Examiner*—Jerry W. Myracle
*Attorney, Agent, or Firm*—Andrus, Sceales, Starke & Sawall

[57] ABSTRACT

An apparatus and method for fatigue stress testing a vehicle wheel or the like includes a plate to which the wheel is mounted, and a clamping system for maintaining the wheel stationary. A nonrotatable shaft is connected to the plate through a bushing. The shaft is connected at a point spaced from the plate to a rotating lateral loading assembly, which rotates relative to the shaft. The lateral loading assembly exerts a lateral force on the shaft simultaneous with rotation of the assembly, so as to cause wobbling of the shaft, which is transferred through the stress plate to the wheel.

17 Claims, 2 Drawing Sheets

APPARATUS AND METHOD FOR FATIGUE TESTING A WHEEL

BACKGROUND AND SUMMARY

This invention relates to an apparatus and method for fatigue testing a vehicle wheel, such as is required of high performance racing wheels Fatigue testing of vehicle wheels is frequently performed by wheel manufacturers to ascertain the number of revolutions the wheel can withstand before failing when a predetermined moment is applied to the wheel. Many of the organizations which govern a particular type of racing set standards for fatigue testing which must be met by a manufacturer's wheels before they can be used in that type of racing.

In the past, machines for fatigue testing vehicle wheels have simulated the action of the wheel on the vehicle. The wheel is mounted to a plate and a predetermined moment is exerted on the plate through a shaft mounted to the plate. The wheel is then spun about an axis coincident with the longitudinal axis of the shaft, which replicates stresses experienced by a wheel as mounted to a vehicle during operation of the vehicle.

The present invention provides an apparatus and method for fatigue testing a vehicle wheel, which also simulates the stresses experienced by a wheel as mounted to a vehicle. In direct contrast to the known testing procedure and apparatus, however, the present invention maintains the wheel stationary during testing. This allows the wheel to be observed and monitored during the test, which may reveal to the manufacturer certain areas of weakness in the wheel not detectable during a test in which the wheel is spun.

In accordance with the invention, an apparatus for fatigue testing a vehicle wheel comprises wheel support means for maintaining the wheel stationary, and fatigue stress inducing means connected to the wheel for inducing stress in the wheel so as to simulate stress induced in the wheel when the wheel is mounted to a vehicle. The wheel support means preferably comprises a wheel supporting plate member to which the wheel is clamped. The fatigue stress inducing means comprises a stress plate to which the wheel is bolted by means of bolt-receiving openings provided in the wheel, and a non-rotatable shaft extending from and interconnected with the stress plate. At least a portion of the shaft is mounted to a lateral loading assembly, which is rotatable relative to the shaft. The lateral loading assembly exerts a force on the shaft in a direction other than in line with the longitudinal axis of the shaft, and preferably in a direction substantially perpendicular thereto. In a preferred embodiment, the lateral loading assembly comprises a bearing member into which at least a portion of the shaft extends, lateral loading means exerting a lateral force on the bearing member which causes the bearing member to move laterally relative to the shaft, and means for imparting rotation to the bearing member when the lateral force is exerted on the bearing member. When the lateral force is exerted on the shaft and the lateral loading assembly is rotated, the shaft is caused to "wobble", which action is transferred through the shaft to the stress plate. Wobbling of the stress plate simulates the relationship of the wheel to a vehicle when the wheel is mounted to the vehicle and the vehicle is operated. The lateral force on the shaft is continuously exerted while the lateral loading assembly rotates so that, in time, the wheel fails due to fatigue loading. Based on the number of revolutions of the lateral loading assembly, the wheel manufacturer can determine whether the wheel conforms to the desired standards.

In a preferred embodiment, the lateral loading assembly comprises a bearing member mounted for slidable lateral movement within a carriage assembly. The carriage assembly is connected to the rotation imparting means for rotating the bearing member. A fluid-operated cylinder assembly is mounted to the carriage assembly, which is operable to selectively exert a lateral force on the bearing assembly. The exertion of a lateral force on the bearing assembly causes the bearing assembly to slide laterally within the carriage assembly, and to laterally deflect the portion of the shaft connected to the bearing assembly due to yielding of the wheel. In a particularly satisfactory construction, fluid pressure is supplied to the fluid-operated cylinder assembly through an internal passage provided in a shaft to which the carriage assembly is connected. A motor or the like is connected to the shaft for imparting rotation thereto, which is transferred through the shaft to the carriage assembly. A conduit extends between the shaft adjacent the carriage assembly and the fluid-operated cylinder for supplying fluid pressure to the cylinder.

Disabling means is preferably provided for disabling the apparatus when a predetermined amount of deflection of the shaft occurs, which corresponds to failure of the wheel.

The invention also contemplates a method of fatigue testing a wheel, substantially in accordance with the foregoing description.

BRIEF DESCRIPTION OF THE DRAWINGS

The drawings illustrate the best mode presently contemplated of carrying out the invention.

In the drawings.

DETAILED DESCRIPTION OF THE PREFERRED EMBODIMENT

Figure 1:
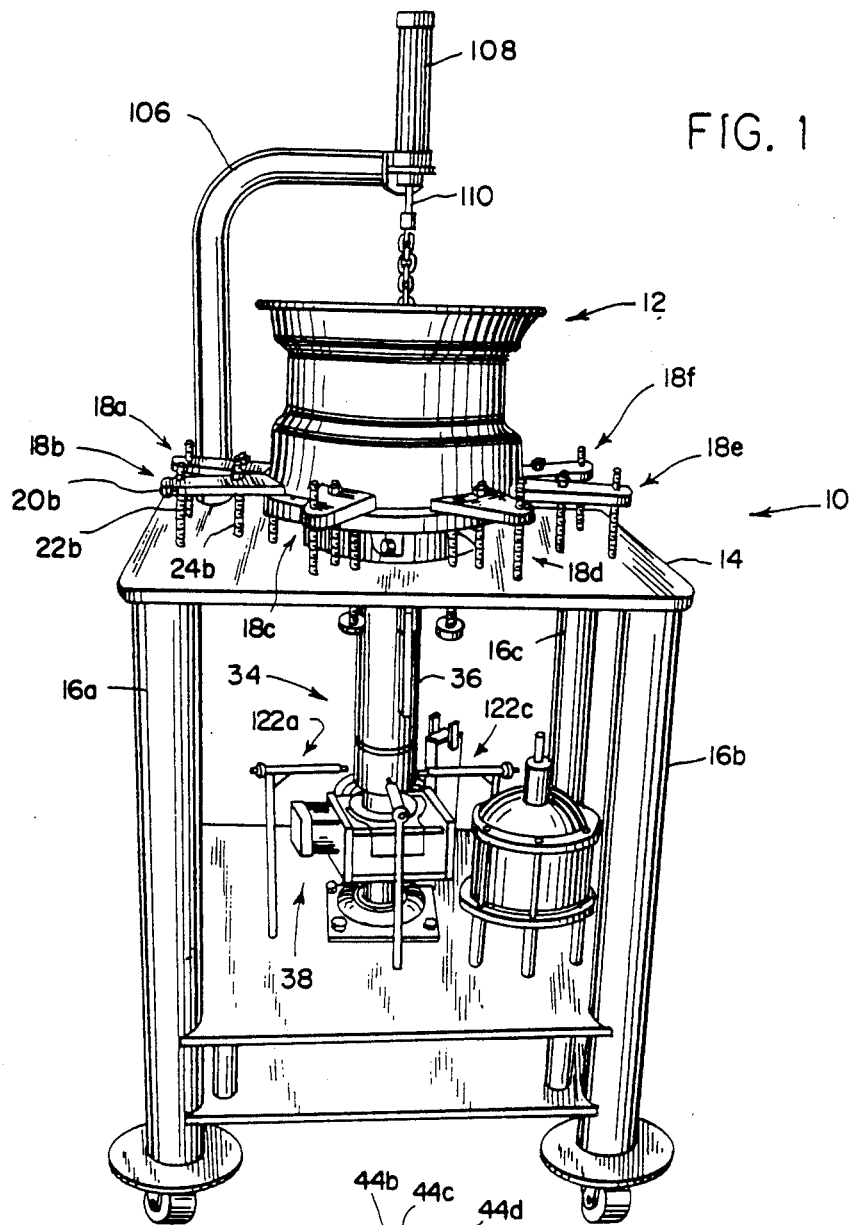
FIG. 1 is a perspective view of the wheel fatigue testing apparatus of the invention, showing a wheel mounted thereto.

As illustrated in FIG. 1, a wheel fatigue testing apparatus, shown at 10, is provided for fatigue testing a vehicle wheel, shown at 12. Wheel 12 as illustrated is a high performance racing wheel, but it is understood that apparatus 10 may be used to test any vehicle wheel or the like which is subjected to rotation during operation and which experiences stresses caused by exertion of a lateral load offset from the wheel.

Apparatus 10 generally includes a wheel clamping stand including a planer upper member 14 and a series of depending legs shown at 16a, 16b, 16c and 16d. Casters are provided at the lower ends of legs 16a–16d for providing movability of apparatus 10.

A series of clamping members 18a, 18b, 18c, 18d, 18e and 18f are connected to upper member 14. Referring to clamping member 18b, each of clamping members 18-18f includes a clamping plate, such as shown at 20b, a threaded spacer such as shown at 22b, and a clamping bolt such as 24b fitted with a nut toward its upper end.

Figure 3:
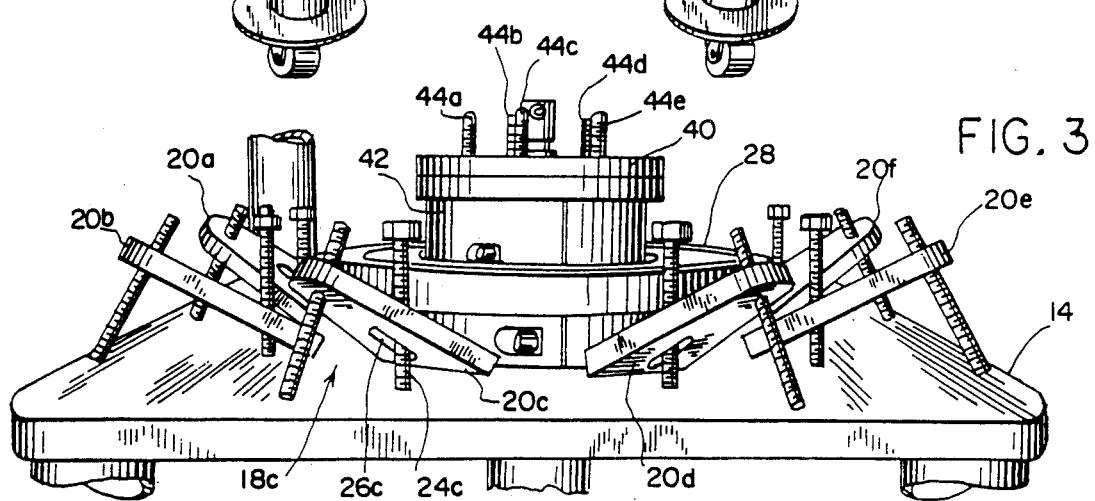
FIG. 3 is a partial perspective view showing the upper portion of the fatigue testing apparatus of FIG. 1, with the wheel removed.

Referring to FIG. 3, clamping members 18a-18f are shown in their disengaged position, wherein wheel 12 is removed from apparatus 10. In FIG. 3, it is seen that each of the clamping bolts, such as shown at 24c, extend through slots such as shown at 26c, provided in the clamping plates, such as shown at 20c. With this arrangement, the clamping plates are movable in an inward and outward manner on the clamping bolts, for accommodating various sizes of wheels mounted to apparatus 10.

Figure 2:
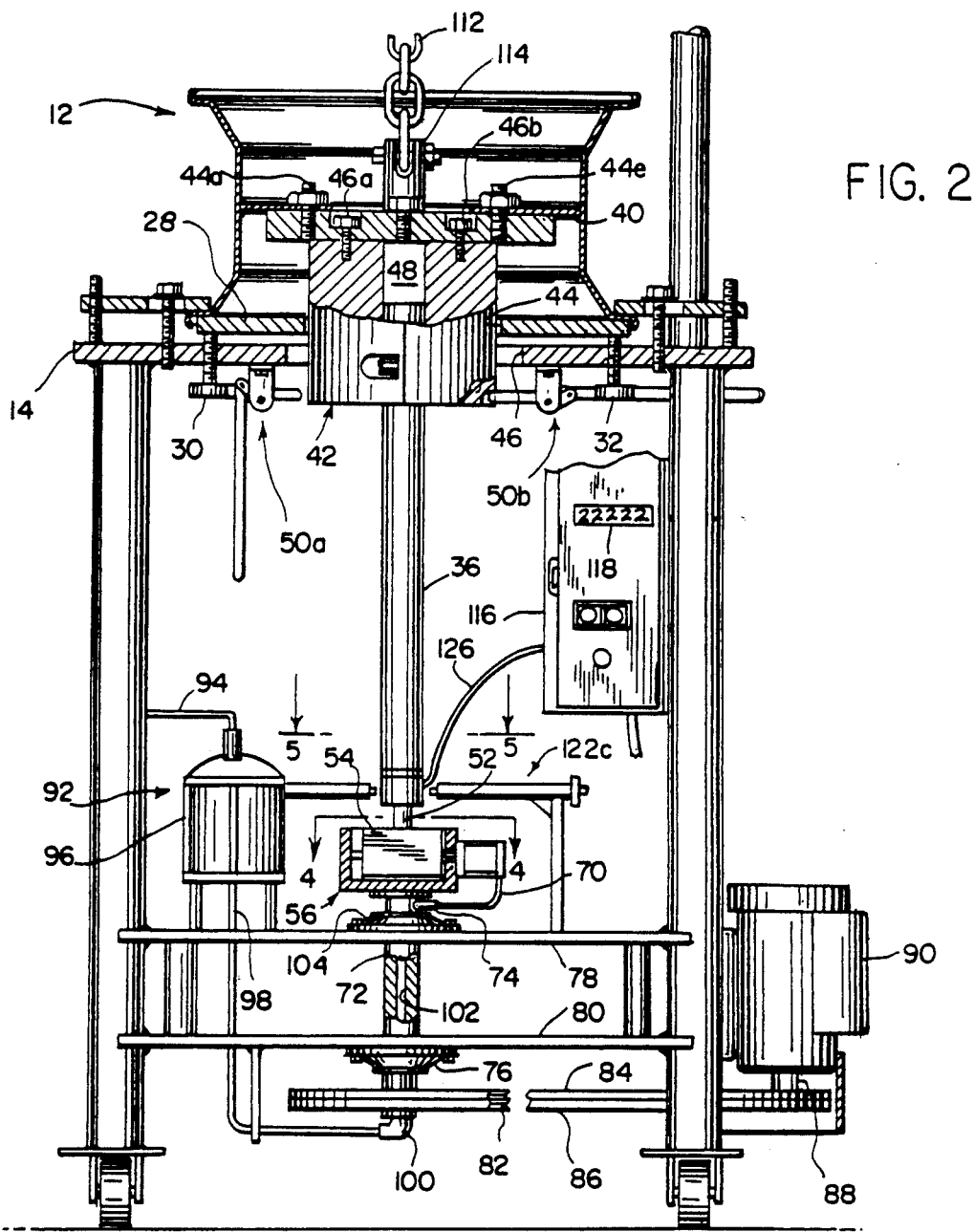
FIG. 2 is a side elevation view, with portions in section, showing the fatigue testing apparatus of FIG. 1.

As also shown in FIG. 3, a wheel supporting plate 28 is connected to and supported by upper member 14. As shown in FIG. 2, wheel 12 is mounted to upper member 14 of apparatus 10 by placing wheel 12 on wheel supporting plate 28. Clamping members 18a-18f are then positioned such that the inwardly facing ends of the clamping plates are positioned against wheel 12, with the horizontal portion of wheel 12 sandwiched between the lower surface of each clamping plate and the upper surface of wheel supporting plate 28. The nuts provided on each of the clamping bolts are then turned down, so as to clamp the rim of wheel 12 to upper member 14.

As also shown in FIG. 2, a series of height adjusting screws, such as shown at 30, 32, support wheel supporting plate 28 above the upper surface of upper member 14. Height adjusting screws 30, 32 allow wheels of varying depths to be satisfactorily mounted to apparatus 10.

Referring to FIG. 1, a fatigue stress inducing assembly 34 extends below upper member 14. Assembly 34 consists generally of a nonrotatable shaft 36, a rotatable lateral loading assembly 38, and a stress plate 40 (FIGS. 2, 3). Stress plate 40 is connected to a conventional split bushing 42, which is disposed between shaft 36 and stress plate 40.

Stress plate 40 is mounted to the hub of wheel 12 in a manner similar to that in which wheel 12 is mounted to a vehicle. Stress plate 40 is provided with a series of upstanding bolts, such as shown at 44a, 44b, 44c, 44d and 44e (FIG. 3). Bolts 44a-44e are arranged in a predetermined bolt pattern corresponding to the pattern of the openings in the hub of wheel 12. As shown in FIG. 3, bolts 44a-44e are arranged in a relatively small diameter pattern. Referring to FIG. 2, however, a somewhat larger stress plate 40 is shown, incorporating bolts such as shown at 44a, 44e in a larger diameter bolt pattern for testing a wheel having a corresponding bolt pattern.

Stress plate 40 is connected to bushing 42 by a series of threaded bolts, such as shown at 46a, 46b in FIG. 2. As shown, bushing 42 extends through an opening 44 formed in wheel supporting plate 28, and an opening 46 formed in upper member 14.

Shaft 36 extends upwardly into a central passage 48 formed in bushing 42, and terminates at a point below the lower surface of stress plate 40.

A series of toggle clamps, two of which are shown at 50a, 50b, are connected to the underside of upper member 14. Toggle clamps 50a, 50b are movable between a release position, in which clamp 50a is shown, and a clamping position, in which clamp 50b is shown. While two toggle clamps are illustrated, it is preferable that four such clamps are provided at equal radial spacing about the outer periphery of bushing 42. Such clamps act to center bushing 42 during operation of apparatus 10.

Figure 4:
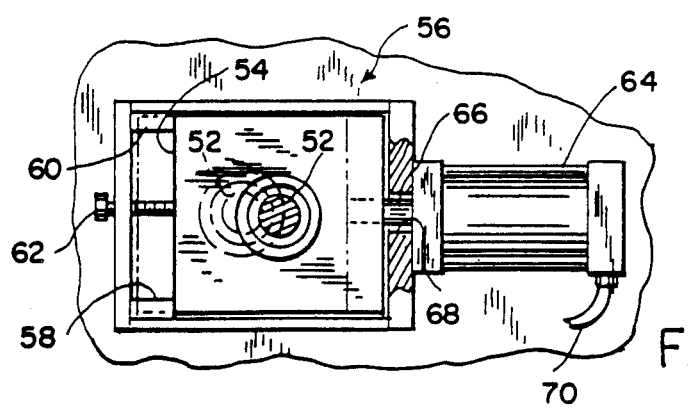
FIG. 4 is a partial sectional view taken generally along line 4—4 of FIG. 2.

The lower end of shaft 36 is provided with a reduced diameter extension portion, shown at 52. As shown in FIGS. 2 and 4, extension portion 52 mates with a female opening provided in a modified pillow block bearing member 54.

Pillow block bearing member 54 is mounted for slidable back and forth movement in a carriage assembly, shown at 56. Carriage assembly 56 comprises a bottom plate member and a series of upstanding walls extending therefrom. Referring to FIG. 4, bearing member 54 is slidably mounted to carriage assembly 56 by means of a pair of gibs shown at 58, 60 which extend inwardly from opposed side walls of carriage assembly 56. A pair of mating slots are formed in the side walls of bearing member 54 adjacent the carriage assembly side walls on which gibs 58, 60 are formed. A centering bolt 62 is provided in a threaded opening formed in an end wall of carriage assembly 56. Centering bolt 62 is adapted to engage bearing member 54 when turned down so as to move rightwardly, to center bearing member 54 relative to shaft 36. After bearing member 54 is centered in this manner, centering bolt 62 is turned so as to move leftwardly, thereby allowing sliding movement of bearing member 54 within carriage assembly 56.

A hydraulic cylinder assembly, shown at 64, is mounted to the end wall of carriage assembly 56 opposite centering screw 62. Cylinder assembly 64 includes an extendible and retractable piston member including a piston rod 66, which extends through an opening 68 formed in the end wall of carriage assembly 56 to which cylinder assembly 64 is mounted. Piston rod 66 is extendible upon supply of hydraulic pressure through a hydraulic line 70 to cylinder assembly 64, for moving piston rod 66 leftwardly. Such movement of piston rod 66 exerts a lateral force on the lower end of shaft 36, which is transferred through bushing 42 and stress plate 40 to the hub of wheel 12. This causes the hub of wheel 12 to yield, which results in sliding movement of bearing member 54 within carriage assembly 56, to a leftward position shown in FIG. 4 in phantom. Turning centering screw 62 so that it moves rightwardly causes bearing assembly 54 to return to its rightwardmost position, and retraction of piston rod 66 within cylinder assembly 64.

Referring to FIG. 2, carriage assembly 56 is mounted to the upper end of a shaft 72, which is rotatably supported by a pair of bearing assemblies 74, 76 mounted to plates 78, 80, respectively. A driven pulley 82 is mounted to the lower end of shaft 72, and a pair of V-belts 84, 86 are trained about pulley 82 and a drive pulley connected to the output shaft 88 of an electric motor 90. In a known manner, operation of motor 90 drives belts 84, 86 and pulley 82, thereby imparting rotation to shaft 72. Such rotation of shaft 72 causes rotation of carriage assembly 56.

A hydraulic pressure source, shown at 92, is mounted to the upper surface of plate 78. Hydraulic pressure source 92 is preferably an air over hydraulic system, in which pressurized air is supplied through an air line 94 to a body portion 96. An outlet line 98 extends from body portion 96, and transfers hydraulic fluid pressure therefrom in response to the supply of pressurized air. Line 98 is connected to a rotary valve 100, which is in communication with an internal central passage 102 formed in shaft 72. In this manner, supply of hydraulic fluid pressure from line 98 through valve 100 is transferred through passage 102, and through a fitting 104 which communicates such fluid pressure from internal passage 102 to hydraulic line 70 interconnected with cylinder assembly 64. With this arrangement, hydraulic fluid pressure is supplied to hydraulic cylinder assembly 64 while carriage assembly 56 and hydraulic cylinder assembly 64 are being rotated by the drive arrangement described above.

Referring to FIGS. 1 and 2, an upstanding arm 106 extends above upper member 14. A pneumatic cylinder assembly 108 is connected to the end of arm 106, and includes an extendible and retractable piston rod 110. Piston rod 110 is connected to the upper end of a multi-link chain 112, which is connected at its lower end to a lug 114 attached to the upper surface of stress plate 40. Upon supply of air pressure to pneumatic cylinder assembly 108 so as to cause retraction of piston rod 110, an upward force is exerted on stress plate 40 through lug 114 and chain 112. The amount of the upward force exerted on stress plate 40 through chain 112 is approximately equal to the weight of the components which are suspended from the hub of wheel 12, namely stress plate 40, bushing 42 and shaft 36. In this manner, the weight of such components does not affect the stress induced in wheel 12 during operation of apparatus 10.

In operation, apparatus 10 functions as follows. Wheel 12 is first positioned on wheel supporting plate 28 and clamped thereto by means of clamping members 18a–18f. The hub of wheel 12 is bolted to stress plate 40 by means of bolts such as 44a, 44e extending upwardly from stress plate 40. Centering pin 62 is turned into carriage assembly 56 so as to cause bearing member 54 to assume its full rightwardmost position within carriage assembly 56, shown in solid lines in FIG. 4. Centering bolt 62 is then moved leftwardly out of engagement with bearing member 54, in an amount sufficient to allow full leftward movement of bearing member 54 within carriage assembly 56. Through a control panel 116 (FIG. 2), motor 90 is actuated so as to impart rotation to shaft 72 through the pulley and belt drive system. This rotation of shaft 72 causes rotation of carriage assembly 56 and hydraulic cylinder assembly 64. Extension portion 52 of shaft 36 is disposed within the bearing passage of bearing member 54, and accordingly no rotation is imparted to shaft 36. When it is desired to initiate the fatigue stress test of wheel 12, a button on panel 116 is depressed so as to actuate an air compressor (not shown), which supplies pressurized air through air line 94 to hydraulic pressure source 92. This results in the output of fluid pressure from hydraulic pressure source 92, through line 98. The pressurized fluid flows through rotary valve 100 and central passage 102 formed in shaft 72, through fitting 104 and hydraulic line 70 to hydraulic cylinder assembly 64. In a known manner, such supply of hydraulic fluid pressure to hydraulic cylinder assembly 64 causes extension of piston rod 66 associated therewith. Appropriate hydraulic valving is provided so that a predetermined force is exerted through piston rod 66 on bearing member 54. The force exerted on bearing member 54 by piston rod 66 causes bearing member 54 to slide leftwardly within carriage assembly 56 due to yielding of the hub of wheel 12, so that the center of extension portion 52 of shaft 36 is moved leftwardly relative to its original position. The leftward position of extension portion 52 is shown in phantom in FIG. 4. When this occurs, and carriage assembly 56 continues to be rotated, a rotating lateral force is exerted on shaft 36 at extension portion 52. This rotating lateral force causes shaft 36 to wobble, which action is transferred through bushing 42 to stress plate 40, and accordingly to the hub of wheel 12. Control panel 116 includes a counter, shown at 118, which counts the revolutions of carriage assembly 56. In this manner, it can be ascertained how many revolutions of carriage assembly 56 take place before fatigue stress failure of wheel 12 induced by stress plate 40.

Figure 5:
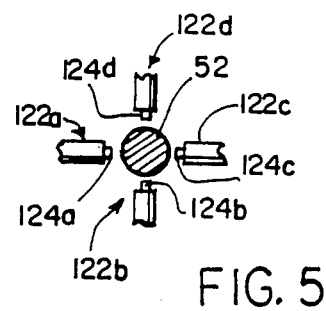
FIG. 5 is a partial sectional view taken generally along line 5—5 of FIG. 2.

When wheel 12 begins to fail, the force exerted on extension portion 52 of shaft 36 by piston rod 66 will cause additional leftward sliding movement of bearing member 54 in carriage assembly 56. When this occurs, a disabling mechanism is provided for shutting down apparatus 10 when the lower end of shaft 36 moves laterally an amount sufficient to indicate failure of wheel 12. This mechanism comprises a series of sensors, shown in FIGS. 1, 2 and 5 at 122a, 122b, 122c and 122d. Each of sensors 122a–122d includes a contact member 124a, 124b, 124c and 124d, respectively. Contact members 124a–124d are wired into a disabling circuit, which is capable of shutting down motor 90. An electrical lead 126, which is interconnected with the disabling circuit, extends between control panel 11 and the lower end of shaft 36 immediately above extension portion 52. Electrical lead 126 supplies an electrical potential to the lower portion of shaft 36. Each of contact members 124a–124d is also supplied with an electrical potential. When wheel 12 fails and the lower end of shaft 36 begins to deflect a sufficient amount so as to cause the outer surface of shaft 36 to come into contact with contact members 124a–124d upon rotation of carriage assembly 56, such contact completes the disabling circuit so as to shut down motor 90. In this manner, the system can be left unattended, while counter 118 provides an accurate count of revolutions prior to failure of wheel 12.

Various alternatives and embodiments are contemplated as being within the scope of the following claims particularly pointing out and distinctly claiming the subject matter regarded as the invention.

I claim:

1. An apparatus for fatigue testing a vehicle wheel, comprising:
    wheel support means for maintaining said wheel stationary; and
    fatigue stress-inducing means connectable to said wheel for inducing stress in said wheel in a manner so as to stimulate stress induced in said wheel when said wheel is mounted to a vehicle, comprising:
    means for applying a moment to said wheel;
    means for rotating said moment applying means; and
    means for varying the moment applied to said wheel during rotation of said moment applying means.

2. The apparatus of claim 1, wherein said wheel support means comprises a wheel-supporting plate member onto which said wheel is adapted to be placed, and clamping means for engaging said wheel and forcing said wheel against said wheel-supporting plate member.

3. The apparatus of claim 2, wherein said clamping means comprises a series of radially spaced clamping members.

4. The apparatus of claim 1, wherein said moment applying means comprises a non-rotatable shaft extending from a stress plate and connectable to said wheel, and lateral loading means for exerting a force on said shaft in a direction other than in line with the longitudinal axis of said shaft, and wherein said means for rotating said moment applying means comprises means for rotating said lateral loading means about said shaft for causing said shaft to wobble, which action is transferred through said stress plate to said wheel to induce stress in said wheel.

5. The apparatus of claim 4, wherein said lateral loading means exerts a force on said shaft in a direction substantially perpendicular to the longitudinal axis of said shaft at a point spaced from said plate for causing said shaft to wobble during rotation of said lateral loading means.

6. The apparatus of claim 5, wherein said lateral loading means comprises a bearing member into which at least a portion of said shaft extends, means acting on said bearing member for exerting a lateral force on said bearing member, and means for imparting rotation to said bearing member when said lateral force is exerted on said bearing member.

7. The apparatus of claim 6, wherein said bearing member is mounted for slidable lateral movement within a carriage assembly, and wherein said lateral force exerting means comprises a selectively actuable fluid-operated cylinder assembly mounted to said carriage assembly for selectively causing lateral sliding movement of said bearing within said carriage assembly.

8. The apparatus of claim 7, wherein said carriage assembly is connected to said rotation imparting means for rotating said bearing member, and wherein said rotation imparting means comprises a rotatably mounted shaft connected at one end to said carriage assembly, and a selectively actuable motor drivingly engaged with said shaft for imparting rotation thereto.

9. The apparatus of claim 8, wherein said shaft is provided with an internal longitudinally extending passage, and wherein fluid pressure is supplied to said cylinder assembly by means of a pressurized fluid supply connected to an end of said shaft and in communication with the internal passage of said shaft, and a conduit extending from said shaft adjacent said carriage for communicating between said passage and said fluid operated cylinder assembly.

10. An apparatus for fatigue testing a vehicle wheel, comprising:
wheel support means for maintaining said wheel stationary;
fatigue stress inducing means connected to said wheel for inducing stress in said wheel in a manner so as to simulate stress induced in said wheel when said wheel is mounted to a vehicle, comprising a plate member to which said wheel is stationarily mounted, a shaft member extending from and interconnected with said plate member, and rotatable lateral loading means acting on said shaft to induce stress on said wheel through said plate member, wherein an electrical potential is supplied to at least a portion of said shaft member; and
means responsive to a predetermined amount of yielding of said wheel for automatically disabling said apparatus upon failure to said wheel, comprising a plurality of sensors placed adjacent the electrified portion of said shaft and spaced radially thereabout, each said sensor being interconnected in an electrical disabling circuit, and wherein failure of said wheel causes said shaft to deflect laterally sufficiently to contact one or more of said sensors for completing said disabling circuit and disabling said apparatus.

11. A method of fatigue testing a vehicle wheel, comprising the steps of:
mounting said wheel to a structure for maintaining said wheel stationary;
applying a moment to said wheel;
rotating said moment to simulate stress in said wheel when said wheel is mounted to a vehicle; and
varying the moment applied to said wheel during rotation of said moment.

12. The method of claim 11, wherein the step of applying a moment to said wheel comprises interconnecting a shaft member with said wheel, exerting a lateral load on said shaft member at a point spaced from said wheel by means of a lateral loading assembly, and rotating said lateral loading assembly while said lateral load is exerted on said shaft member, so that the rotating lateral load exerted on said shaft is transferred to said wheel for inducing fatigue stress in said wheel.

13. The method of claim 12, further comprising the step of sensing a predetermined deflection of said shaft member corresponding to failure of said wheel, and automatically cutting of rotation of said lateral loading assembly in response thereto.

14. An apparatus for fatigue testing a vehicle wheel, comprising:
wheel support means for maintaining said wheel stationary; and
fatigue stress-inducing means connectable to said wheel for inducing stress in said wheel in a manner so as to simulate stress induced in said wheel when said wheel is mounted to a vehicle, comprising:
a stress plate member to which said wheel is connectable by means of fasteners extending through a series of openings provided in the hub of said wheel; and
stress inducing means acting on said stress plate to stress said wheel through said plate, comprising a nonrotatable shaft extending from said stress plate, and lateral loading means rotatable relative to said shaft, comprising a bearing member into which at least a portion of said shaft extends and means acting on said bearing member for exerting a lateral force on said bearing member, wherein said lateral loading means exerts a force on said shaft in a direction substantially perpendicular to the longitudinal axis of said shaft at a location spaced from said plate, and means for rotating said lateral loading means relative to said shaft comprising means for imparting rotation to said bearing member when said lateral force is exerted on said bearing member for causing said shaft to wobble, which action is transferred through said stress plate to said wheel to induce stress in said wheel.

15. The apparatus of claim 14, wherein said bearing member is mounted for slidable lateral movement within a carriage assembly, and wherein said lateral force exerting means comprises a selectively actuable fluid-operated cylinder assembly mounted to said carriage assembly for selectively causing lateral sliding movement of said bearing within said carriage assembly.

16. The apparatus of claim 15, wherein said carriage assembly is connected to said rotation imparting means for rotating said bearing member, and wherein said rotation imparting means comprises a rotatably mounted shaft connected at one end to said carriage assembly, and a selectively actuable motor drivingly engaged with said shaft for imparting rotation thereto.

17. The apparatus of claim 16, wherein said shaft is provided with an internal longitudinally extending passage, and wherein fluid pressure is supplied to said cylinder assembly by means of a pressurized fluid supply connected to an end of said shaft and in communication with the internal passage of said shaft, and a conduit extending from said shaft adjacent said carriage for communicating between said passage and said fluid operated cylinder assembly.

* * * * *